United States Patent
Trimble

(10) Patent No.: US 8,333,981 B2
(45) Date of Patent: Dec. 18, 2012

(54) ANTIFUNGAL TREATMENT OF NAILS

(75) Inventor: John Olin Trimble, Texarkana, TX (US)

(73) Assignee: Humco Holding Group, Inc., Texarkana, TX (US)

( * ) Notice: Subject to any disclaimer, the term of this patent is extended or adjusted under 35 U.S.C. 154(b) by 0 days.

(21) Appl. No.: 12/246,382

(22) Filed: Oct. 6, 2008

(65) Prior Publication Data

US 2009/0092576 A1    Apr. 9, 2009

Related U.S. Application Data

(60) Provisional application No. 60/998,199, filed on Oct. 9, 2007.

(51) Int. Cl.
| | |
|---|---|
| A01N 25/24 | (2006.01) |
| A61K 8/18 | (2006.01) |
| A61K 49/08 | (2006.01) |
| A61K 47/00 | (2006.01) |
| A61Q 3/02 | (2006.01) |

(52) U.S. Cl. ........... 424/400; 424/61; 424/9.2; 514/770; 514/947

(58) Field of Classification Search .................. None
See application file for complete search history.

(56) References Cited

U.S. PATENT DOCUMENTS

| | | | |
|---|---|---|---|
| 5,322,689 | A | 6/1994 | Hughes et al. |
| 5,696,164 | A | 12/1997 | Sun et al. |
| 5,814,305 | A | 9/1998 | Laugier et al. |
| 5,993,790 | A | 11/1999 | Strauss et al. |
| 6,042,845 | A | 3/2000 | Sun et al. |
| 6,143,793 | A | 11/2000 | Laugier et al. |
| 6,224,887 | B1 | 5/2001 | Samour et al. |
| 6,284,258 | B1 | 9/2001 | Rose et al. |
| 6,284,802 | B1 * | 9/2001 | Bissett et al. |
| 6,296,838 | B1 | 10/2001 | Bindra et al. |
| 6,372,234 | B1 | 4/2002 | Deckers et al. |
| 6,455,592 | B1 | 9/2002 | Laugier et al. |
| 6,495,124 | B1 | 12/2002 | Samour et al. |
| 6,676,953 | B2 | 1/2004 | Hexamer et al. |
| 7,048,913 | B2 | 5/2006 | Hexamer et al. |
| 7,074,392 | B1 | 7/2006 | Friedman et al. |
| 2005/0208110 | A1 | 9/2005 | Singh et al. |
| 2006/0057075 | A1 | 3/2006 | Arkin et al. |
| 2006/0182766 | A1 * | 8/2006 | Modi |
| 2008/0207537 | A1 * | 8/2008 | Turner et al. |

FOREIGN PATENT DOCUMENTS

| | | |
|---|---|---|
| EP | 1138314 | 10/2001 |
| GB | 2 124 485 A | 2/1984 |
| WO | WO 97/42934 | 11/1997 |
| WO | WO/02/22115 | 3/2002 |

OTHER PUBLICATIONS

Rowe et al. (Eds.), Handbook of Pharmaceutical Excipients, 5th Edition, 2006, "Bentonite", pp. 58-60, "Hydroxypropyl Cellulose", pp. 336-340, and "Hypromellose", pp. 346-349.*

Aly, R. 1999. Ecology, epidemiology and diagnosis of tinea capitis. Pediat Inf. Dis J. 18:180-185.
Aly, R., R. J. Hay, A. Del Palacio, and R. Galimberti. 2000. Epidemiology of tinea capitis. Med Mycol. 38:183-188.
Aman, S., T. S. Haroon, I. Hussain, M. A. Bokhari, and K. Khurshid. 2001. Tinea unguium in Lahore, Pakistan. Med Mycol. 39:177-180.
British Journal of Dermatology, vol. 85 Issue 5 p. 437-449, Nov. 1971.
Chem Pharm Bull (Tokyo). Nov. 1998; 46(11):1797-802.
Indian J Pathol Microbio. Apr. 2002; 45(2):169-72.
Int J Pharm. Oct. 1, 2002; 245(1-2):25-36.
International Journal of Pharmaceutics, Mar. 6, 2007; 322(1-2):196-201.
Journal of the American Podiatric Medical Association, vol. 89, Issue 3 124-130, 1999.
J Invest Dermatol. Feb. 1981; 76(2):76-9.
J Pharm Pharmacol. Jan. 1983; 35(1):28-33.
J Pharm Pharmacol. Nov. 1985; 37(11):771-5.
J Pharm Pharmacol. Mar. 1999; 51(3):271-8.
Nail Swelling as a Pre-formulation Screen for the Selection and Optimisation of Ungual Penetration Enhancers, Journal of Pharmaceutical Research, Jul. 2007, pp. 2207-2212.
Ramsewak RS, et al. In vitro antagonistic activity of monoterpenes and their mixtures against 'toe nail fungus' pathogens. Phytother Res. Apr. 2003; 17(4):376-9.
Robbins CR.Chemical & Physical behavior of human nail, 3rd edition, New York: Springer-verlag 1997 pp. 93-130.
Thymus Vulgaris. PDR for Herbal Medicine. Montvale, NJ: Medical Economics Company. p. 1184.
Weitzman, I., and R. C. Summerbell. 1995. The dermatophytes. Clin Microbiol Rev. 8:240-59.
Mohorcic et al., "An investigation into keratinolytic..", Int'l Jour. of Pharmaceutics, Elsevier BV, NL, vol. 332, No. 1-2, Feb. 13, 2007, pp. 196-201, ISSN 0378-5173.
Greeves, M. Bontanical.com, "Thyme, Garden. Botanical: Thymus Vulgaris (Linn.) Family: N.O. Labiale." [online], 1995-2010 [retrieved on Jul. 23, 2010]. Retrieved from the Internet: http://www.botanical.com/botanical/mgmh/t/thygar16.html, pp. 1-9 of 9.
International Search Report and Written Opinion, European Patent Office, Jan. 7, 2009, Application No. PCT/US2008/078960.
European Patent Office, Official Action, Serial No. 08837880.7, May 20, 2010.
European Patent Office, Response to Official Action, Serial No. 08837880.7, Jun. 24, 2010.

* cited by examiner

Primary Examiner — Jeffrey S. Lundgren
Assistant Examiner — Gregg Polansky
(74) Attorney, Agent, or Firm — Jackson Walker L.L.P.

(57) ABSTRACT

A fungus treatment composition used to deliver active drugs trans-nail as well as a method for producing the fungus treatment composition, which may contain up to 50% additive ingredients. Preferred embodiments of the invention may include fungus treatment compositions which provide high nail penetrating power, which have antifungal agents, which have antifungal essential oils, which have optimum drying and barrier properties, which have pharmaceutically elegant properties, or most preferably an embodiment having a total combination thereof.

8 Claims, 5 Drawing Sheets

ANTIFUNGAL TREATMENT OF NAILS

This application claims priority to U.S. Provisional Patent Application Ser. No. 60/998,199, entitled "ANTIFUNGAL TREATMENT OF NAILS" filed on Oct. 9, 2007, the entire content of which is hereby incorporated by reference.

BACKGROUND

The present invention relates to a method for the topical treatment of fungal diseases in nails. This invention relates in particular to a composition for enhancing the permeation rate of antifungal agents in nails and to an apparatus adapted for use with the testing of the invention.

All living things can be classified into one of five fundamental kingdoms of life and the term fungus refers generically to all members of the Kingdom Fungi. There are more than a million species of fungi but only about 400 cause diseases relevant to man.

Infections of the nail are so important that they get their own name. The term onychomycosis is used both to refer to non-dermatophyte nail infections and to any fungal nail infection caused by any fungus. The term tinea unguium can be applied only if the infection is due to a dermatophyte. The distinction is narrow and technical. The leading yeast cause of onychomycosis is candida albicans. It is not uncommon to have more than one fungus species jointly causing the infection.

The dermatophytes are not a particular fungus but rather a common short-hand label for a group of three genera of fungi that commonly cause skin disease of people:
  (a) *Epidermophyton floccosum* is a common cause of dermatophytosis in otherwise healthy individuals. It infects skin and nails. The infection is restricted to the nonliving cornified layers of epidermis since the fungus lacks the ability to penetrate the viable tissues of the immunocompetent host (Aman, S., T. S. Haroon, I. Hussain, M. A. Bokhari, and K. Khurshid. 2001. Tinea unguium in Lahore, Pakistan. Med Mycol. 39:177-180). Disseminated infections due to any of the dermatophytes are very unlikely due to the restriction of the infection to keratinized tissues. *Epidermophyton floccosum* infections are communicable and usually transmitted by contact.
  (b) *Trichophyton* is a causative agent of dermatophytosis and infects the skin and nails (Aly, R., R. J. Hay, A. Del Palacio, and R. Galimberti. 2000. Epidemiology of tinea capitis. Med Mycol. 38:183-188). *Trichophyton* is a keratinophilic filamentous fungus. Ability to invade keratinized tissues and the possession of several enzymes are the major virulence factors of these fungi (Weitzman, I., and R. C. Summerbell. 1995. The dermatophytes. Clin Microbiol Rev. 8:240-59).
  (c) *Microsporum* is a genus that causes dermatophytosis. Dermatophytosis is a general term used to define the infection in skin or nails due to any dermatophyte species. *Microsporum* has the ability to degrade keratin and thus can reside on skin and its appendages and remains noninvasive. Proteinases and elastases of the fungus may act as virulence factors. *Microsporum* spp. mostly infects the skin. Nail infections are very rare. The pathogenesis of the infection depends on the natural reservoir of the species. Geophilic spp. is acquired via contact with soil. Zoophilic species are transmitted from the infected animal. Direct or indirect human-to-human transmission is of concern for anthropophilic species. Asymptomatic carriage may be observed. Otherwise healthy hosts are infected (Aly, R. 1999. Ecology, epidemiology and diagnosis of tinea capitis. Pediat Inf. Dis J. 18:180-185).

Candida is thin-walled yeast that reproduces by budding. No more than ten species of Candida cause disease in humans with any frequency even though there are more than 150 species (Kwon-Chung, K. J., and J. E. Bennett. 1992. Medical Mycology. Lea & Febiger, Philadelphia).

Cutaneous candidiasis is arguably the most common form of candidiasis. The infection involves the very outer-most layers of the skin. Healthy skin is quite resistant to candidal infection and in essentially all cases a predisposing factor is present. These forms of localized candiasis can be very irritating to the patient although neither invasive nor life-threatening. The most common and important form of candidal skin infections is erosio interdigitalis blastomycetica in the finger or toe webspace with eroded erythematous area surrounded with macerated skin.

Antifungal Agents

There are a number of topical agents used in treatment of superficial cutaneous mycoses. The superficial cutaneous mycoses that respond to topical therapy include the localized infections of nails and epidermis due to the dermatophytes and Candida. These topical agents are of distinct chemical classes. The major characteristics of the currently available topical antifungal agents that are in general effective in treatment of superficial cutaneous mycoses and/or candidiasis are shown below:
  (a) Amphotericin B—indicated for cutaneous candidiasis.
  (b) Nystatin—indicated for cutaneous candidiasis.
  (c) Clotrimazole—indicated for dermatophytosis and cutaneous candidiasis.
  (d) Econazole—indicated for dermatophytosis and cutaneous candidiasis.
  (e) Ketoconazole—indicated for dermatophytosis and cutaneous candidiasis.
  (f) Miconazole—indicated for dermatophytosis and cutaneous candidiasis.
  (g) Oxiconazole—indicated for dermatophytosis and cutaneous candidiasis.
  (h) Sulconazole—indicated for dermatophytosis and cutaneous candidiasis.
  (i) Butenafine HCl—indicated for dermatophytosis.
  (j) Naftifine—indicated for dermatophytosis.
  (k) Terbinafine—indicated for dermatophytosis.
  (l) Ciclopirox olamine—indicated for dermatophytosis and cutaneous candidiasis.
  (m) Haloprogin—indicated for dermatophytosis and cutaneous candidiasis.
  (n) Tolnaftate—indicated for dermatophytosis.
  (o) Undecylenate—indicated for dermatophytosis.

Antifungal aromatic molecules that make up chemotyped essential oils are shown below:
  (a) Phenols
    i. Thymol: *Trachyspermum ammi* (Ajowan)
    ii. Carvacrol: *Origanum compactum* (Oregano)
      *Origanum heracleoticum* (Greek Oregano)
      *Corydothymus capitatus* (Spanish Oregano)
      *Satureja montana* (Winter or mountain savory)
      *Thymus serpyllum* (Wild thyme or mother-of-thyme)

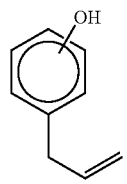

(b) Terpenic Alcohols
  i. Linalool: *Aniba rosaeodora* (Rosewood)
     *Coriandrum sativum* (Coriander)
  ii. Geraniol: *Cymbopogon martinii* (Palmarosa)
  iii. Thujanol: *Origanum majorana* (Sweet marjoram or oregano)
  iv. Borneol: *Thymus satureioides* (Thym borneol-carvacrol type)
     *Inula graveolens* (Sweet inula)
  v. Menthol: *Mentha* x *piperita* (Peppermint)
     *Mentha arvensis* (Field mint or cornmint)
  vi. Citronnellol: *Pelargonium asperum* (Geranium)
  vii. Terpineneol: *Melaleuca altemifolia* (Tea Tree)
     *Origanum majorana* (Sweet marjoram or oregano)
  viii. α-Terpineol: *Ravensara aromatica* (Ravensara)
     *Eucalyptus radiata* (Black or peppermint eucalyptus)

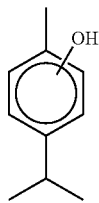

(c) Aromatic Aldehydes
  i. Cinnamaldehyde: *Cinnamomum verum* (Ceylon cinnamon)
     *Cinnamomum cassia* (Chinese cinnamon)
     *Cinnamomum loureirii* (Vietnamese cinnamon)
  ii. Cuminal: *Cuminum cyminum* (Cumin)
     *Eucalyptus polybractea* (Blue or mallee eucalyptus)
  iii. Phellandral: *Eucalyptus polybractea* (Blue or mallee eucalyptus)

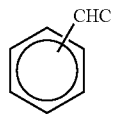

Thymol is known as a powerful antifungal. The essential oil of common thyme is made up of 20-55% thymol (Thymus Vulgaris. PDR for Herbal Medicine. Montvale, N.J.: Medical Economics Company. p. 1184). It was used to medicate bandages before the advent of modern antibiotics (Grieve, Maud (Mrs.). Thyme. A Modern Herbal. Hypertext version of the 1931 edition. Accessed: Dec. 14, 2006). It has also been shown to be effective against the fungus that commonly infects toenails (Ramsewak R S, et al. In vitro antagonistic activity of monoterpenes and their mixtures against 'toe nail fungus' pathogens. Phytother Res. 2003 April; 17 (4):376-9).

Oregano oil is antifungal. It has been tested against a variety of microorganisms and is found to exert a high degree of anti-fungal actions ("The Cure is in the Cupboard: How to Use Oregano for Better Health" by Dr. Cass Ingram). Oregano is perhaps the most powerful herbal anti-fungal agent known. Its effectiveness is enhanced by its safety since it is non-toxic. Oregano is such a potent anti fungal agent that it is capable of destroying even resistant fungal forms such as the mutated fungi which result from antibiotic therapy.

Menthol penetrates into the nail to kill the fungal elements that cause damage. Workers at the Department of Horticulture and National Food Safety and Toxicology Center at Michigan State University have studied the antifungal effects of Menthol. They proved that Menthol specifically inhibits the growth of a multitude of fungi known to cause onychomycosis (Phytother Res. 2003 April; 17 (4):376-9).

Tea-tree oil is a known antifungal with activity against various infectious organisms. Tea-tree has been tested against 58 disease causing fungal organisms. These are the same fungi thriving within the toenail. 57 isolates were inhibited by tea-tree.

Eucalyptus oil is known as a powerful antifungal. It is excellent for Athletes Foot and other fungal infections. Eucalyptus leaves were crushed by the Aborigines to heal wounds and fight infection.

Camphor has little or no detectable anti-fungal activity. A composition of 4% Menthol with 2% Camphor is significantly more potent in its ability to kill toenail fungus. The camphor also likely acts as a penetration agent allowing better access of the Menthol to the fungus under the toenail bed (International Patent No. WO/2002/022115 to McKenzie, et al., issued Mar. 21, 2002).

Several different compositions for fungus treatments have been described.

U.S. Pat. No. 5,696,164 to Sun, et al., issued Dec. 9, 1997, discloses a method for the treatment of fungal diseases in nails, which comprises the topical administration to the nail and, if desired, also to the surrounding skin, of (1) a sulfhydryl containing amino acid or a derivative thereof, the pharmaceutically acceptable salts or esters thereof, or stereoisomers thereof, (2) urea, (1) and (2) being administered in an amount sufficient to enhance the permeation of antifungal drugs through nail tissue, either prior to or, preferably, concurrently with the topical administration to the nail of (3) an effective amount of an antifungal drug. There is also disclosed a bandage adapted for the topical administration of medication to the nail, said bandage comprising a T-shaped adhesive backing, and a flexible pad having an impervious backing and a nail-shaped cavity backed by said impervious backing, wherein said nail-shaped cavity contains absorptive means having absorbed therein urea and a sulfhydryl containing amino acid or a derivative thereof, a pharmaceutically acceptable salt or ester thereof, or a stereoisomer thereof.

U.S. Pat. No. 5,814,305 to Laugier, et al., issued Sep. 29, 1998, describes the improved penetration of antifungal agents through the nails using hydrophilic penetration agents customarily used for the transcutaneous penetration of active ingredients. A corresponding dermatological composition contains at least one antifungal agent chosen, in particular, from among those of the allylamine family, such as terbinafine-HCl and naftifine-HCl; at least one hydrophilic penetration agent chosen, in particular, from among the glycols, glycol monoethers, glycol diethers, dimethylsulphoxide, caprolactam, dimethylisosorbide, isopropylidene glycerol, dimethylimidazolidinone, ethyl lactate, the polyoxyethylenated $C_8$-$C_{10}$ glycerides, polyethylene glycol 20 glyceryl laurate and dimethylacetamide; and a water-alcohol solvent medium which dissolves the said antifungal agent(s) and in which the said penetration agent(s) is (or are) at least partially miscible.

U.S. Pat. No. 5,993,790 to Strauss, et al., issued Nov. 30, 1999, discloses a composition comprising water based nail lacquer and urea, which is useful in the partial or complete evulsion of the nails, and in the treatment of fungal, yeast and bacterial infections of the nails and the nail beds. Also disclosed are methods for evulsing nails, and for treating antifungal and antibacterial infections, comprising the administration of the composition of the invention to the toenails or fingernails of a mammal.

U.S. Pat. No. 6,042,845 to Sun, et al., issued Mar. 28, 2000, discloses a method for the treatment of fungal diseases in nails, which comprises the topical administration to the nail and, if desired, also to the surrounding skin, of (1) a sulfhydryl containing amino acid or a derivative thereof, the pharmaceutically acceptable salts or esters thereof, or stereoisomers thereof, (2) urea, (1) and (2) being administered in an amount sufficient to enhance the permeation of antifungal drugs through nail tissue, either prior to or, preferably, concurrently with the topical administration to the nail of (3) an effective amount of an antifungal drug. There is also disclosed a bandage adapted for the topical administration of medication to the nail, said bandage comprising a T-shaped adhesive backing, and a flexible pad having an impervious backing and a nail-shaped cavity backed by said impervious backing, wherein said nail-shaped cavity contains absorptive means having absorbed therein urea and a sulfhydryl containing amino acid or a derivative thereof, a pharmaceutically acceptable salt or ester thereof, or a stereoisomer thereof.

U.S. Pat. No. 6,143,793 to Laugier, et al., issued Nov. 7, 2000, describes the improved penetration of antifungal agents through the nails using hydrophilic penetration agents customarily used for the transcutaneous penetration of active ingredients. A corresponding dermatological composition contains at least one antifungal agent chosen, in particular, from among those of the allylamine family, such as terbinafine-HCl and naftifine-HCl; at least one hydrophilic penetration agent chosen, in particular, from among the glycols, glycol monoethers, glycol diethers, dimethylsulphoxide, caprolactam, dimethylisosorbide, isopropylidene glycerol, dimethylimidazolidinone, ethyl lactate, the polyoxyethylenated $C_8$-$C_{10}$ glycerides, polyethylene glycol 20 glyceryl laurate and dimethylacetamide; and a water-alcohol solvent medium which dissolves the said antifungal agent(s) and in which the said penetration agent(s) is (or are) at least partially miscible.

U.S. Pat. No. 6,224,887 to Samour, et al., issued May 1, 2001, discloses a nail lacquer effective for the treatment or prevention of fungal infections, such as, onychomycosis, which includes a fungicidally effective amount of ciclopirox, econazole, or other antifungal agent in a clear, stable, film-forming lacquer vehicle which includes a water-insoluble film-forming polymer; 2-n-nonyl-1,3-dioxolane or similar penetration enhancer; and volatile solvent. A plasticizer for the film-forming polymer which is also compatible with the other components may be included although the preferred penetration enhancers may also function as plasticizer. The composition, when applied to the nails provides a hard, clear, water-resistant film containing the antifungal agent. The film is resistant to multiple washings and is effective in the treatment of onychomycosis.

U.S. Pat. No. 6,284,258 to Rose, et al., issued Sep. 4, 2001, discloses compounds that are two-part molecules, and compositions containing such compounds, in which one part is designed to become covalently bonded to the skin (bonding agent) and the other part (a characteristic use agent) is designed to impart some characteristic use, such as emolliency, moisturizing effect, anti-acne, anti-wrinkle, anti-pain, antimicrobial, antifungal, antiviral, anti-irritation, skin tanning and skin lightening effects, extended protection of the skin (e.g., from ultraviolet light, by incorporation of a sunscreen component; from toxic and/or irritating substances; from insects and skin parasites, by incorporation of insecticides and/or insect repellants; from free radicals or other agents, as in aging, by incorporation of antioxidants), or dyeing of hair, skin nails, wool or fur. The covalently bonded part may also be useful to impart skin strengthening effect (e.g., from shear forces) or as wound healing agents.

U.S. Pat. No. 6,296,838 to Bindra, et al., issued Oct. 2, 2001, discloses an antifungal composition for the treatment of human nails containing extracts of walnut hull, pulverized roots of *Nardostachys jatamansi* or *Vetiveria zizanioides* or *Catharanthus roseus*, polyols, fixed oil, non-ionic emulsifiers, thickening agent plasticizer and base. The invention also relates to a process for the preparation of the above synergistic composition.

U.S. Pat. No. 6,455,592 to Laugier, et al., issued Sep. 24, 2002, describes the improved penetration of antifungal agents through the nails using hydrophilic penetration agents customarily used for the transcutaneous penetration of active ingredients. A corresponding dermatological composition contains at least one antifungal agent chosen, in particular, from among those of the allylamine family, such as terbinafine-HCl and naftifine-HCl; at least one hydrophilic penetration agent chosen, in particular, from among the glycols, glycol monoethers, glycol diethers, dimethylsulphoxide, caprolactam, dimethylisosorbide, isopropylidene glycerol, dimethylimidazolidinone, ethyl lactate, the polyoxyethylenated $C_8$-$C_{10}$ glycerides, polyethylene glycol 20 glyceryl laurate and dimethylacetamide; and a water-alcohol solvent medium which dissolves the said antifungal agent(s) and in which the said penetration agent(s) is (or are) at least partially miscible.

U.S. Pat. No. 6,495,124 to Samour, et al., issued Dec. 17, 2002, discloses a nail lacquer for the treatment or prevention of fungal infections, such as, onychomycosis, which includes fungicidally effective amount of ciclopirox, econazole, or other antifungal agent in a compatible film-forming lacquer vehicle which includes a water-insoluble film-forming polymer; pentadecalactone, or similar cyclic lactone compound or derivative thereof, and volatile solvent. The pentadecalactone functions as a plasticizer for the film-forming polymer and as a penetration enhancer for the antifungal agent. The composition, when applied to the nails provides a hard, clear, water-resistant film containing the antifungal agent. The compositions are used for the treatment of onychomycosis.

U.S. Pat. No. 6,676,953 to Hexamer, et al., issued Jan. 13, 2004, discloses an antifungal composition for the treatment of fungal infections in, around and under human nails, in which the composition comprises an aqueous solution of a wetting agent such as alcohol and a source of fluoride ions sufficient to establish a pH ranging from about 2.8 to about 3.5 in the composition. A preferred source of fluoride ions is stannous fluoride or stannous fluoride in an amount sufficient to saturate the solution. According to the method of the invention, one or more drops of the subject solution are topically applied to the infected nail and surrounding cuticular area periodically until the infection abates.

U.S. Pat. No. 7,048,913 to Hexamer, et al., issued May 23, 2006, discloses an antifungal composition for the treatment of fungal infections in, around and under human nails, in which the composition comprises an aqueous solution of a wetting agent such as alcohol and a source of fluoride ions sufficient to establish a pH ranging from about 2.8 to about 3.5 in the composition. A preferred source of fluoride ions is stannous fluoride or stannous fluoride in an amount sufficient to saturate the solution. According to the method of the invention, one or more drops of the subject solution are topically applied to the infected nail and surrounding cuticular area periodically until the infection abates.

U.S. Pat. No. 7,074,392 to Friedman, et al., issued Jul. 11, 2006, discloses a topical sustained release delivery system for delivery of antifungal agents to the finger or toenails achieving high penetration through the nails by combining the antifungal agent with a keratolytic agent and a humectant. The pharmaceutical sustained release topical preparation is provided in a varnish or spray form for treating the nail and surrounding tissues, where the active ingredient is an antifungal agent, a keratolytic agent, or preferably a combination of an antifungal and a keratolytic agent. The composition may further comprise an antibacterial, an antiviral, an antipsoriatic agents, or combinations thereof.

Pfizer manufactures the prescription antifungal agent, fluconazole. This product is trademarked as DIFLUCAN (fluconazole tablets, Pfizer, New York). It is for the treatment of oropharyngeal and esophageal candidiasis. Fluconazole is also effective for the treatment of serious systemic candidal infections, including urinary tract infection, peritonitis and pneumonia.

Schering manufactures the prescription antifungal antibiotic, griseofulvin. This product is trademarked as FULVICIN (griseofulvin, Schering-Plough, Kenilworth, N.J.). It is orally effective against superficial infections caused by those fungi responsible for dermatomycoses in man and animals, namely: *M. canis, M. gypseum, M. audouini, E. floccosum, T. tonsurans, T. rubrum, T. mentagrophytes, T. megninii, T. gallinae, T. verrucosum, T. sulfureum, T. interdigitale, T. schoenleinii, T. crateriform*. Griseofulvin is inactive against: *C. albicans* (monilia), *C. neoformans, B. dermatitidis, A. israelii, H. capsulatum, C. immitis, M. furfur* (tinea versicolor) and bacteria. The drug is useful in the treatment of fungal infections of the scalp and those of the glabrous skin. The drug is less effective in chronic infections of the feet, palms, and nails. Since these chronic fungal infections tend to cause hyperkeratosis, concomitant topical keratolytic therapy is almost always necessary.

Novartis Pharmaceuticals manufactures the prescription antifungal, terbinafine HCl. This product is trademarked as LAMISIL (terbinafine HCl solution, Novartis, Basel, Switzerland). It is for the treatment of fungal infections of the skin and nails caused by dermatophytes such as *Trichophyton* (e.g., *T. rubrum, T. mentagrophytes, T. verrucosum, T. violaceum*), *M. canis* and *E. floccosum*.

Sanofi-Aventis manufactures the prescription antifungal agent, ciclopirox. This product is trademarked as PENLAC (ciclopirox topical solution, Sanofi-Aventis, Bridgewater, N.J.). It is a component of a comprehensive management program, and is indicated as topical treatment in immunocompetent patients with mild to moderate onychomycosis of fingernails and toenails without lunula involvement, due to *Trichophyton rubrum*. The comprehensive management program includes removal of the unattached, infected nails as frequently as monthly, by a health care professional who has special competence in the diagnosis and treatment of nail disorders, including minor nail procedures.

Janssen-Ortho manufactures the prescription antifungal, itraconazole. This product is trademarked as SPORANOX (itraconazole capsules, Janssen-Ortho, Raritan, N.J.). It is for the treatment of oral and/or esophageal candidiasis in adult HIV-positive or other immunocompromised patients.

Ganeden Biotech, Inc. manufactures the over-the-counter military strength fungus treatment, with 2.0% miconazole nitrate, and the over-the-counter triple action fungus treatment, with 1.0% clotrimazole. These products are trademarked as CLEARLY CONFIDENT (antifungal lotion, Ganeden Biotech, Mayfield Heights, Ohio). The military strength is Emu Oil patented formulation, and the triple action contains benzalkonium chloride, emu oil, and tea tree oil.

Schering-Plough HealthCare Products, Inc. manufactures the over-the-counter fungal nail management kit, with 1.0% tolnaftate. This product is trademarked as DR. SCHOLL'S (fungal nail management kit, Schering-Plough). It contains a nail revitalizer cream, a nail brush applicator, a nail file, and a tolnaftate antifungal cream.

Eulactol USA Inc. manufactures the over-the-counter maximum strength anti-fungal liquid, with 25.0% undecylenic acid. This product is trademarked as FLEXITOL (anti-fungal liquid, Eulactol USA Inc., Boca Raton, Fla.). It contains nature's healers, tea tree oil, aloe vera and vitamin E.

Alva manufactures the over-the-counter extra strength anti-fungal liquid, with 12.5% undecylenic acid, and the over-the-counter professional formula anti-fungal liquid, with 15.0% undecylenic acid. These products are trademarked as FUNGICURE (anti-fungal liquid, Alva, Niles, Ill.). Both the extra strength and the professional formula contain aloe and vitamin E.

Kramer Laboratories, Inc. manufactures the over-the-counter double strength anti-fungal solution, with 25.0% undecylenic acid. This product is trademarked as FUNGI NAIL (anti-fungal solution, Kramer Laboratories, Inc. Miami Fla.).

Woodward Laboratories manufactures the over-the-counter antifungal treatment, with 1.0% tolnaftate. This product is trademarked as MYCOCIDE NS (antimicrobial nail solution, Woodward Laboratories, Aliso Viejo, Calif.). It contains a patented penetrating delivery system and the soothing allantoin difference.

NDC Laboratories manufactures the over-the-counter medical strength antifungal solution, with 1.0% clotrimazole. This product is trademarked as RECLEAR AF (antifungal solution, NDC Laboratories, Anaheim, Calif.).

Del Laboratories, Inc. manufactures the over-the-counter antifungal liquid, with 25.0% undecylenic acid. This product is trademarked as SALLY HANSEN NO MORE FUNGUS (antifungal liquid, Del Laboratories, Inc., New York, N.Y.).

Blaine Labs, Inc. manufactures the over-the-counter antifungal cream, with 10.0% undecylenic acid. This product is trademarked as TINEACIDE (antifungal cream, Blaine Labs, Inc. Santa Fe Springs, Calif.).

Almost all of the above commercial products to treat onychomycosis including ciclopirox, clotrimazole, fluconazole, griseofulvin, itraconazole, miconazole nitrate, terbinafine HCl, tolnaftate, and undecylenic acid have problems.

Ciclopirox reportedly has only a 14% cure rate after several months of use. Up to 48 weeks of daily applications with ciclopirox topical solution and professional removal of the unattached nail are considered the full treatment needed to achieve a clear or almost clear nail (PENLAC Nail Lacquer (ciclopirox) Topical Solution, 8% Prescribing Information).

Clotrimazole reportedly has only 30.55% of dermatophyte isolates being sensitive (Indian J Pathol Microbio. 2002 April; 45 (2):169-72).

Fluconazole reportedly is effective only for the treatment of serious systemic candidal infections. Sixteen percent of over 4000 patients treated with fluconazole in clinical trials of 7 days or more experienced adverse events (DIFLUCAN (fluconazole) Capsule Prescribing Information).

Griseofulvin reportedly has poor cure rates and requires 10-18 months of use. The drug is less effective in chronic infections of the nails. Concomitant topical keratolytic therapy is almost always necessary since these chronic fungal infections tend to cause hyperkeratosis (FULVICIN (griseofulvin) Tablet Prescribing Information).

Itraconazole reportedly is unsafe for patients with compromised liver function or patients with gastroesophageal reflux disease on a proton pump inhibitor. The total observed incidence of adverse events that are possibly or directly drugrelated during treatment or within 14 days post-treatment for itraconazole oral solution is 18.2% (SPORANOX (itraconazole) Oral Solution Prescribing Information).

Miconazole nitrate reportedly has low permeation through the lipids in the human nail plate (J Pharm Pharmacol. 1999 March; 51 (3):271-8).

Terbinafine HCl reportedly presents problems with drug interactions and liver toxicity. The plasma clearance of terbinafine may be accelerated by drugs which induce metabolism and may be reduced by drugs which inhibit cytochrome P450. Clinical studies in patients with liver dysfunction and impaired renal function suggest that the elimination rate of orally administered terbinafine may be reduced in these patients (LAMISIL (terbinafine HCl) Tablet Prescribing Information).

Tolnaftate reportedly has only 47.22% of dermatophyte isolates being sensitive (Indian J Pathol Microbio. 2002 April; 45 (2):169-72).

Undecylenic acid reportedly has low permeation through the lipids in the human nail plate (J Pharm Pharmacol. 1999 March; 51 (3):271-8).

The present invention overcomes many of these problems. None of these references suggest or disclose the use of a combination of nail penetrating agents, over-the-counter antifungal agents, antifungal essential oils, drying and barrier agents, and pharmaceutical elegance agents. This combination is particularly advantageous because it unexpectedly increases the penetration of the active antifungal agent through the nail and thus provides better pharmacological action.

Nail Permeation Systems

Antifungals can be dissolved in penetration enhancers that have superior nail penetration and are able to be delivered to the site of infection. Little correlation is found between transdermal enhancers and those that enhance nail absorption.

The permeability coefficient of water is $16.5 \times 10(-3)$ cm h-1 and that for n-octanol is $0.27 \times 10(-3)$ cm h-1 (J Pharm Pharmacol. 1983 January; 35 (1):28-33). Permeability coefficients are uniformly about five-fold smaller when the alcohols are undiluted than when they are applied in water (J Pharm Pharmacol. 1985 November; 37 (11):771-5).

Water solubility of the drug is an important consideration in formulating a topical product for nail disorders since water solubility can enhance maximum drug flux. Water-soluble miconazole reportedly has 75% of dermatophyte isolates being sensitive (Indian J Pathol Microbio. 2002 April; 45 (2): 169-72).

An understanding of the nail disulphide links allows drug delivery strategies based on the chemical alteration of the nail barrier. Penetration enhancers containing thiol groups such as acetylcysteine are the most promising for nail drug delivery (Academy of Pharmaceutical Sciences Conference, 2005).

A 10-month clinical study of a unique antimicrobial nail solution containing allantoin determines its effectiveness against pedal onychomycosis. 79.8% of the nails have severe disease at the start of the study and 32.6% of the patients' nails have severe disease by the conclusion of the study (Journal of the American Podiatric Medical Association, Vol 89, Issue 3 124-130, 1999).

Nail swelling is identified as a simple technique to evaluate penetration enhancers. Thioglycolic acid produces the greatest nail weight increase of $71.0 \pm 4.6\%$ (Nail Swelling as a Pre-formulation Screen for the Selection and Optimisation of Ungual Penetration Enhancers, Journal of Pharmaceutical Research, July 2007).

Urea is thought to promote penetration through the nail by tertiary structure and possibly secondary linkage in keratin. Compounds such as urea are known to be denaturating agents that result in disruption of the water structure around proteins and promote unfolding and dissociation of the protein molecules (Robbins C R. Chemical & Physical behavior of human nail, 3rd edition, New York: Springer-verlag 1997 pp-93-130).

Preparation of Fungus Treatment

Fungus treatment may be prepared by suspending additives within an aqueous Magnesium Aluminum Silicate phase using a high-shear mixing method. Suspension Phase: charge kettle with Purified Water; install mixer; turn on the mixer; with mixing, add VEEGUM HS (magnesium aluminum silicate, R.T. Vanderbilt Co., Inc., Norwalk, Conn.); mix for 30 minutes or until dissolved. Aqueous Phase: turn on the sweep mixer and add Propylene Carbonate, Propylene Glycol, PRIMAFLO HP22 (hydroxypropylcellulose, Ashland Aqualon, Wilmington, Del.), EDTA, Miconazole Nitrate, Allantoin, and Sodium Thioglycolate. Oil Phase: in same kettle, add SD-40B Alcohol; turn on the mixer; add Camphor, Eucalyptus Oil, Menthol, Urea, Oregano Oil, Tea Tree Oil, Thymol, and Acetylcysteine, and mix until dissolved. Final Phase: in same kettle, with mixing, add 50% Sodium Hydroxide; homogenize for 20 minutes.

A magnesium aluminum silicate suspension is composed of natural smectite clays that have been water-washed to optimize purity and performance. The value of suspensions like magnesium aluminum silicate as stabilizing and rheological agents is due to their colloidal structure in water. Water penetrates the area between the smectite platelets and forces them further apart. The weakly positive platelet edges are attracted to the negatively charged platelet faces once the smectite is hydrated. The colloidal structure also provides yield value. A greater yield value means a more stable suspension.

The suspension phase must be properly dispersed and hydrated to provide the desired performance properties. Any materials present in the purified water when VEEGUM HS is added will interfere with hydration and inhibit the formation of the desired colloidal structure. A greater degree of hydration means a stronger colloidal structure and a greater yield value. The degree of hydration is directly proportional to the amount of energy used to disperse the product and therefore increases in proportion to the following factors:
  a. Mixing Time
  b. Mixing Intensity
  c. Water Temperature The aqueous phase can be combined with the following water-miscible solvents:
  (a) Up to 30% Propylene Carbonate
  (b) Up to 30% Propylene Glycol
  (c) Up to 20% SD-40B Alcohol The oil phase is suspended and separated by the smectite colloidal structure. This structure reduces the tendency of emulsions to thin out and break at elevated temperatures since smectite viscosity is not affected by heat. It will stabilize emulsions containing the following oil-miscible additives:
  (a) Eucalyptus Oil
  (b) Oregano Oil
  (c) Tea Tree Oil The oil phase is synergistic with the smectite colloidal structure. The viscosity and stability of such mixtures is greater than the viscosity and stability of the same formulation made with the individual components of the mixture. Advantages of combining the smectite colloidal structure with the oil phase are:
(a) Increased Economical Use
(b) Increased Yield Value
(c) Increased Temperature Stability
(d) Decreased Tacky Application The chemical composition of nail and experimental evidence indicate that the aqueous pathway plays a dominant role in drug penetration into nail. Water is the principal plasticizer for the nail. This aqueous fungus treatment hydrates hard nail plates and they become softer and more flexible.

Characteristics of Penetration Enhancers

Data suggests that the hydrated human nail plate behaves like a hydrogel of high ionic strength to the polar and semipolar alcohols such as SD-40B Alcohol. Thus it appears that solvents which tend to promote diffusion through the skin horny layer have little promise as accelerants of nail plate permeability. Also, the nail permeability of drugs is found to markedly decrease as their molecular weights increase, i.e., the nail permeability of Itraconazole, with a molecular weight of 706 g/mol, is markedly less than the nail permeability of Miconazole Nitrate, with a molecular weight of 479 g/mol. The drug concentration in the nail plate is also observed to be dependent on the solubility and the flux of the drug, i.e., Miconazole Nitrate with a water solubility of 0.3 mg/mL and an ethanol solubility of 7.6 mg/mL, is more concentrated than Tolnaftate, which is insoluble in water. Attention has to be paid mainly to the formula solubility of the compound in order to screen drugs for potential topical application to the nail plate. Average permeability coefficients of water and ethanol are determined as 16.5+/−5.9×10(−3) cm hr-1 and 5.8+/−3.1×10(−3) cm hr-1 respectively (J Invest Dermatol. 1981 February; 76 (2):76-9).

The weights and stresses of nail pieces are dramatically changed after immersion in aqueous solvents containing Acetylcysteine. This course of penetration through the nail membrane is initially membrane-controlled and later becomes a matrix-controlled process because of the membrane's greater permeability. The fungus treatment formulations enhance nail permeation processes by increasing the concentration of the active agent and therefore therapeutic efficacy (Chem Pharm Bull (Tokyo). 1998 November; 46 (11): 1797-802).

Clinical studies of unique antimicrobial nail solutions containing Allantoin determine its effectiveness against pedal onychomycosis. Rates of clinical and complete cure appear to be higher among patients who undergo Allantoin debridement. The fungus treatment formulations for onychomycosis involve applying antifungal agents concurrently with the Allantoin debridement of the infected nail structures. Studies confirm the excellent safety profile of this topical therapy. There is also high compliance with the regimen. Nails are additionally trimmed (J Am Podiatr Med Assoc. 1999 March; 89 (3): 124-30).

The dense matrix of nail keratin is reduced after treatment with Sodium Thioglycolate. Human nails treated with it in vitro have a 3.8-fold increase in flux compared to the control. Sodium thioglycolate breaks and reforms the covalent disulphide bridges of nail keratin. (British Journal of Dermatology, Volume 85 Issue 5 Page 437-449, November 1971).

Roughness scores indicate a 2-fold increase when the dorsal nail layer is subjected to Urea versus the control. Bioadhesion measurements of films on the human nail substrate are generally higher for these Urea-etched nails than that of the control nails. The in vitro permeability profiles also demonstrate a significant increase in drug permeability compared to control. The corneocyte layers of the dorsal nail disintegrate and the structure markedly loosens during treatment. Drug penetration across nail is improved even more by filing of the impenetrable dorsal surface of the nail. Most structural changes occur in the first 2 weeks. (Int J Pharm. 2002 Oct. 1; 245 (1-2):25-36).

Delivery of Therapeutic Antifungal Agents

A wide range of drug actives have been incorporated for nail absorption, including nail psoriasis and onychomycosis drugs. These drugs require large doses and frequent administration. Systemic administration of antifungal and antipsoriatic drugs is always associated with severe side effects and potential drug interaction risks. Topical delivery is the most desired therapy due to relatively less severe side effects and better patient compliance. This delivery is considered less successful in treating onychomycosis due to poor trans-nail bioavailability of drugs. The major reasons for poor trans-nail absorption includes:
(a) Unfavorable physicochemical properties of the drugs.
(b) Lack of formulations that can overcome the barrier properties of the nail plate.
(c) Short residence time of topical formulations and extensive binding of drug to the nail keratin.

The nail is a good barrier to active drug permeation and active drug flux is known to be low. In vitro permeability profiles demonstrate that nail samples treated with an etchant demonstrate a significant increase in this drug permeability compared to control samples.

Trans-nail delivery has quickly gained acceptance as a unique delivery route providing an alternative to existing oral therapeutic regimens. These topical applications of conventional solutions or creams on the infected nail frequently include the use of bandages to keep these dosage forms in place on the nails.

Trans-nail delivery can be a superior alternative for active drugs which are potent and relatively hydrophilic. The success of these hydrophilic treatments are compromised in that solutions and creams are usually miscible with water or hydrophilic and can consequently be removed from the surface of the nail or be carried away by dissolution out of the nail when washing and thus have to be reapplied.

The absolute bioavailability of a compound delivered trans-nail is generally less than that delivered orally unless the compound is highly metabolized in the liver. Trans-nail delivery may however allow for the administration of drugs that cannot be administered by the oral route due to significant liver or gastrointestinal metabolism.

Fungus treatment is an inorganic suspension that forms a physical barrier. VEEGUM HS is water-washed to optimize purity and performance. Its rheological properties are tailored to optimize drying and barrier properties. This benefit is also synergistic in combination with the polymeric thickener PRIMAFLO HP22.

Water-miscible solvents are often added to fungus treatment as preferred solvent carriers. Propylene Carbonate, Propylene Glycol, and SD-40B Alcohol are naturally derived from petrochemicals.

Oil-miscible additives are powerful essential oils that kill fungi that cause toenail and fingernail infection. Eucalyptus, Oregano, and Tea Tree Oil are essential oils that have been proven to kill fungus. These essential oils can help eliminate nail fungus with none of the dangerous side effects seen in numerous medications and they have been tested in medical labs and proven effective to kill fungus infections.

Specific application instructions include:
(a) Pre-Application—Any loose material is removed using a clipper or file. Rough surfaces are smoothed using an emery board.
(b) Night Application (Preferred)—Nails are first soaked for 10-20 minutes in lukewarm water. Embodiments are spread over entire surface of infection with an applicator brush.
(c) Morning Application (Optional)—Embodiments are removed once daily with alcohol. Affected area is washed. An even layer of embodiments are applied over affected area.

SUMMARY

The present invention relates to a fungus treatment composition, including matrices of an inorganic suspension such as smectite clay. In particular, this invention relates to compositions which may comprise an internal oil phase containing optional antifungal essential oils, and an aqueous phase comprising hydrophilic active drugs.

The current invention comprises a fungus treatment composition which could be used to deliver active drugs trans-nail. The invention further comprises a method for producing the fungus treatment composition, which may contain up to 50% additive ingredients.

Preferred embodiments of the invention may include fungus treatment compositions which provide high nail penetrating power, which have over-the-counter antifungal agents, which have antifungal essential oils, which have optimum drying and barrier properties, which have pharmaceutically elegant properties, or most preferably an embodiment having a total combination thereof.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1:
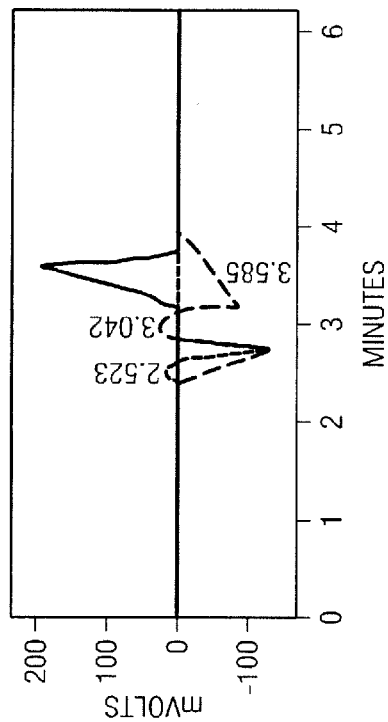
FIG. 1 shows the chromatograms of the total area of UV-absorbing bioavailable compounds of preferred embodiment of the invention ("Fungus Treatment Sample 1A") and a standard antifungal cream ("Fungus Treatment Sample 2A") after 1 week of in-vitro residence time.
Figure 1:
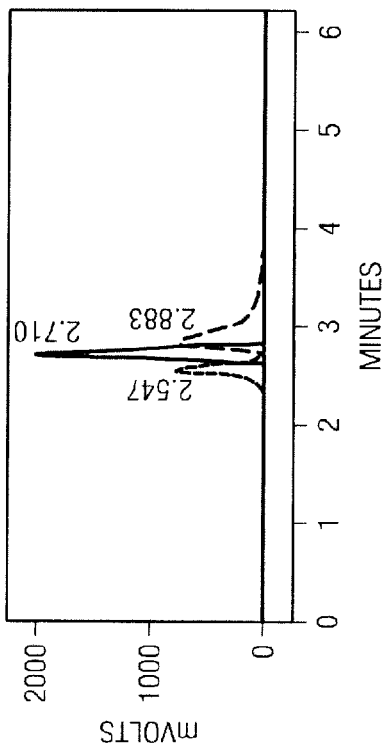
Figure 2:
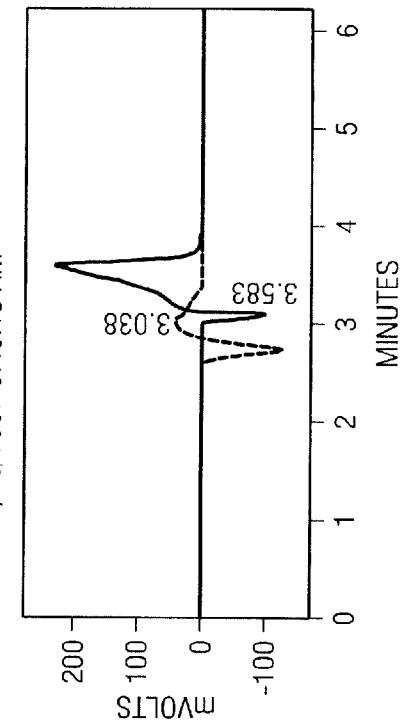
FIG. 2 shows the chromatograms of the total area of UV-absorbing bioavailable compounds of preferred embodiment of the invention ("Fungus Treatment Sample 1B") and a standard antifungal cream ("Fungus Treatment Sample 2B") after 2 weeks of in-vitro residence time.
Figure 2:
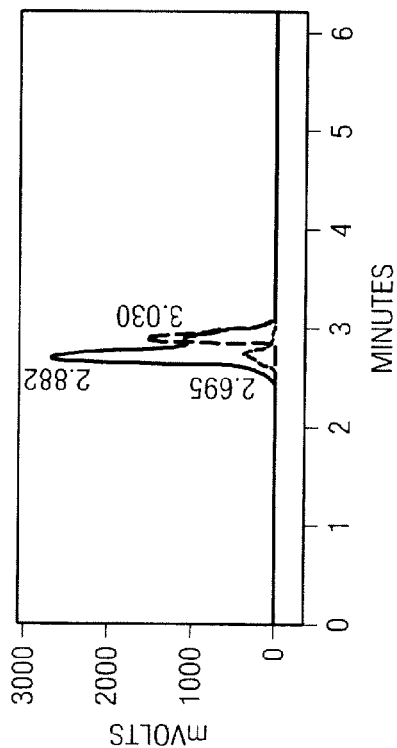
Figure 3:
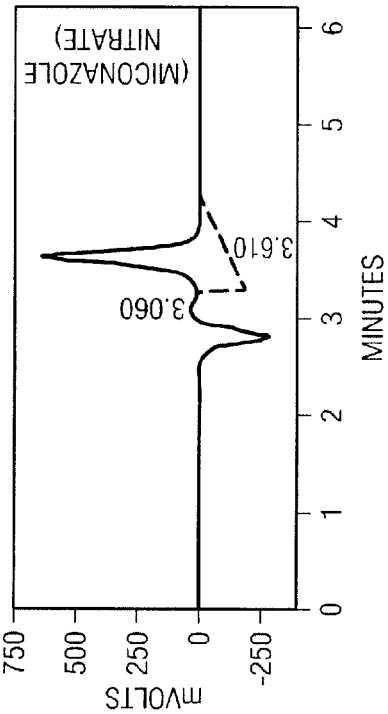
FIG. 3 shows the chromatograms of the total area of UV-absorbing bioavailable compounds of preferred embodiment of the invention ("Fungus Treatment Sample 1C") and a standard antifungal cream ("Fungus Treatment Sample 2C") after 3 weeks of in-vitro residence time.
Figure 3:
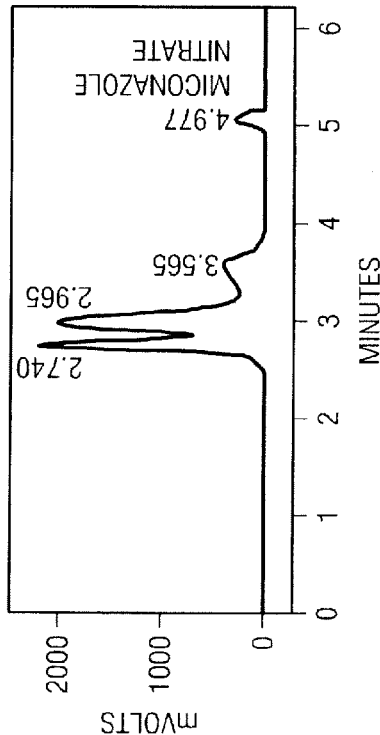
Figure 4:
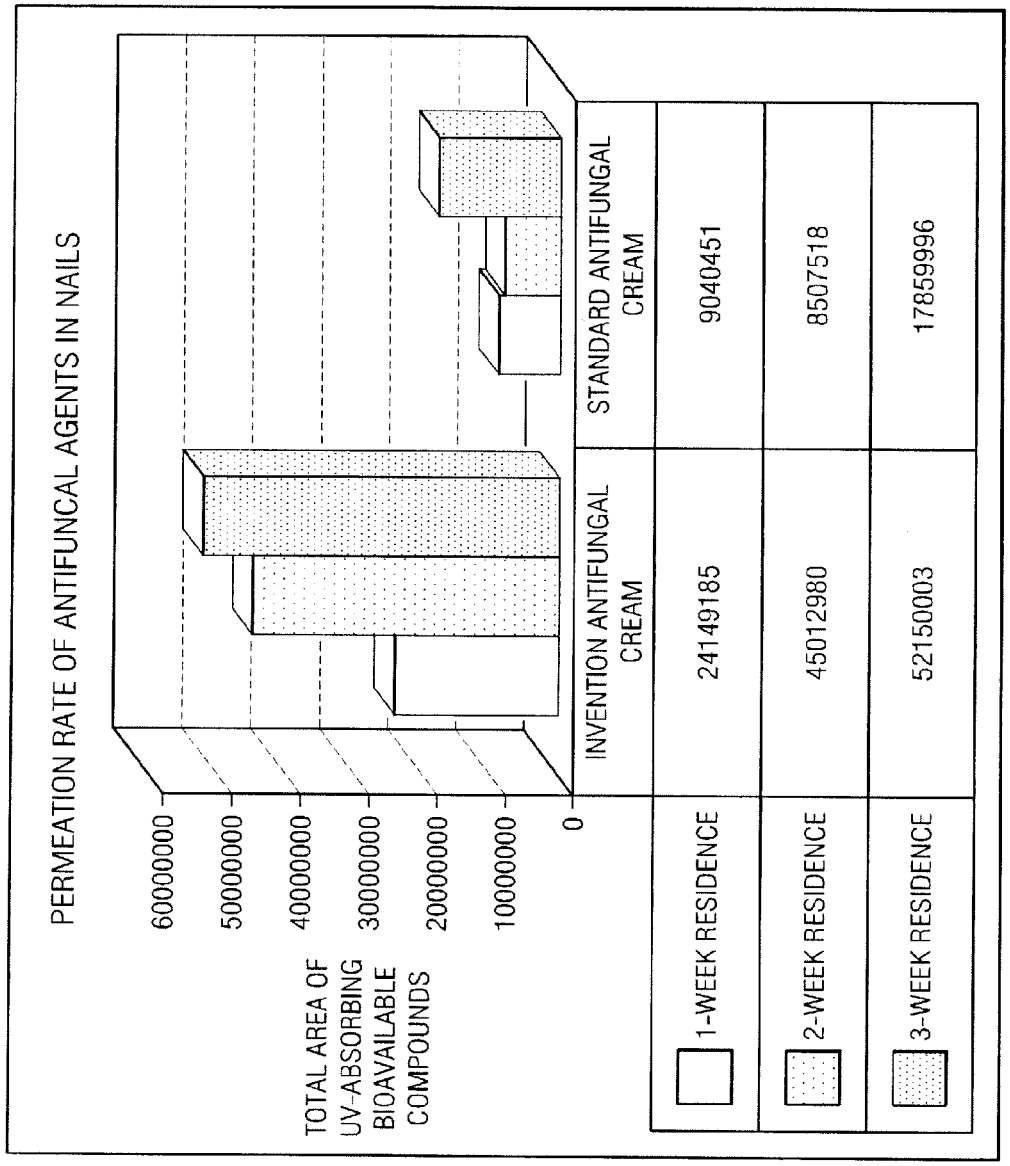
FIG. 4 shows the charts of the total area of UV-absorbing bioavailable compounds versus in-vitro residence time of preferred embodiment of the invention and a standard antifungal cream.
Figure 5:
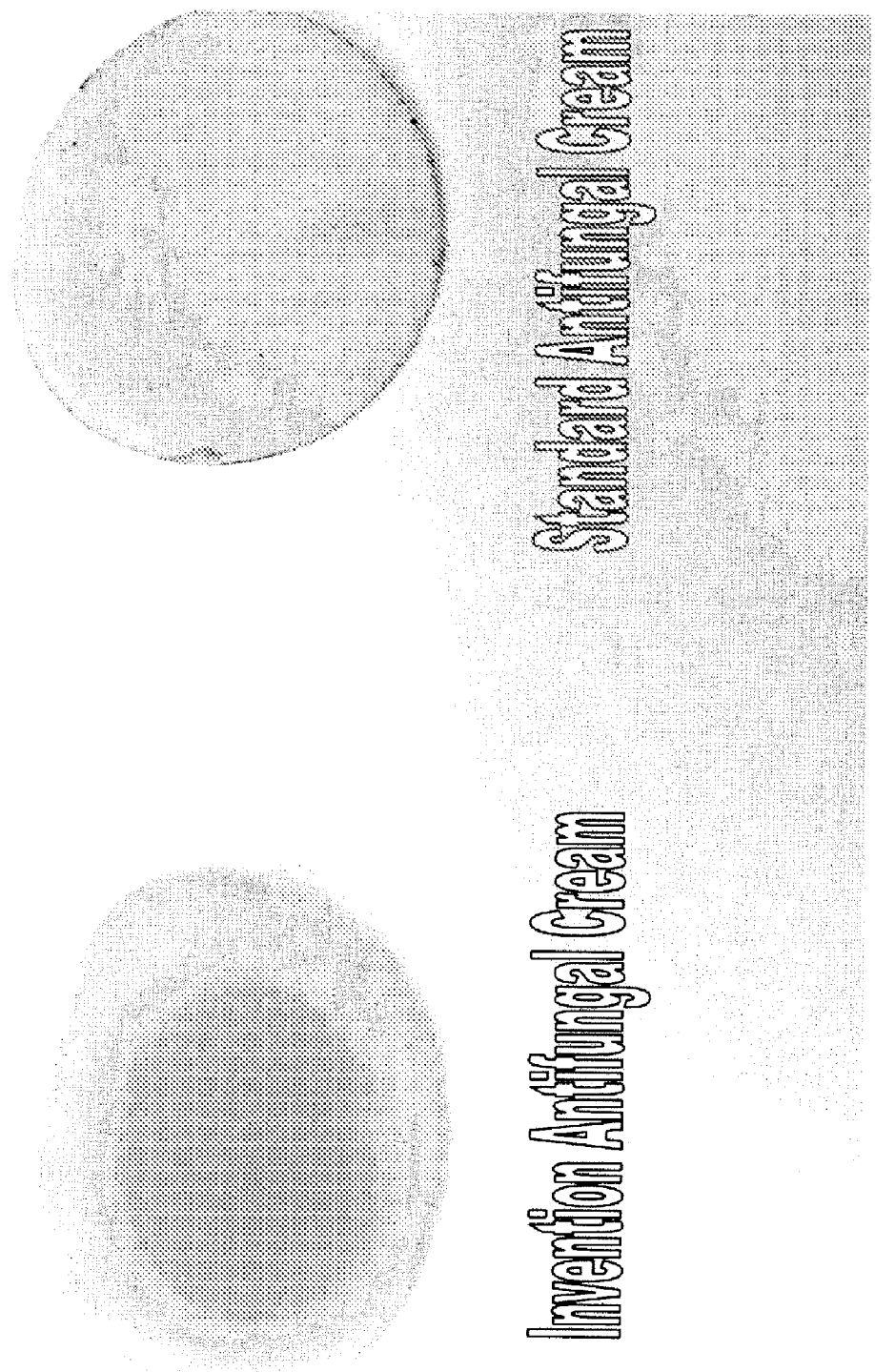
FIG. 5 shows the images of Franz diffusion cell nail pieces after 3 weeks of in-vitro residence time of preferred embodiment of the invention and a standard antifungal cream.

One aspect of the current invention pertains to a fungus treatment composition which may be used to deliver active drugs trans-nail. The invention further comprises a method for producing the fungus treatment composition, which may contain up to 50% additive ingredients. Preferred embodiments of the invention may include fungus treatment compositions which provide high nail penetrating power, which have over-the-counter antifungal agents, which have antifungal essential oils, which have optimum drying and barrier properties, which have pharmaceutically elegant properties, or most preferably an embodiment having a total combination thereof.

Composition

A preferred embodiment of the fungus treatment composition comprises smectite clay, preferably magnesium aluminum silicate, most preferably a pharmaceutical grade of magnesium aluminum silicate with maximum electrolyte stability and minimum acid demand.

Examples of smectite clays may include montmorillonite and bentonite. The smectite clay may be present in a concentration range of 3.5% to 6.5%, preferably 4.0% to 6.0%, most preferably 4.5% to 5.5%.

The extent to which smectite clay particles are delaminated into individual platelets is referred to as the degree of hydration. The greater the degree of hydration, the stronger the colloidal structure, and the greater the viscosity and yield value of the dispersion.

This embodiment of the invention further comprises water-miscible solvent, preferably aqueous-alcoholic-miscible solvent, and most preferably aqueous-alcoholic-miscible solvent with solubility in from about 1 percent to about 20 percent of aqueous alcohol. Examples of water-miscible solvent includes ethylene glycol, 1,2-propylene glycol, 1,3-propanediol, 1,2-butylene glycol, 2,3-butylene glycol, 1,4-butanediol, 1,2-hexylene glycol, diethylene glycol, dipropylene glycol, polyethylene glycol, polypropylene glycol, glycerin, trimethylolpropane, pentaerythritol, sorbitol, diethyl carbonate, diisopropyl carbonate, dibutyl carbonate, ethylene carbonate, propylene carbonate (1,2-propylene carbonate), 1,2-butylene carbonate, 2,3-butylene carbonate, methanol, ethanol, 1-propanol, 2-propanol, 2-methyl-1-propanol, 1-butanol, 2-butanol, 2-methyl-2-propanol, 2-propene-1-ol, 2-propyn-1-ol, 2-methoxy-1-ethanol, 1-methoxy-2-propanol, and 2-methoxy-1-propanol, or a mixture thereof The water-miscible solvent may be present in a concentration range of 5% to 30%, preferably 10% to 25%, most preferably 15% to 20%.

This embodiment further comprises a water-soluble polymer suspension of hydroxypropylcellulose, such as PRIMA-FLO HP22 (Chemical nature: Water-soluble polymer suspension, INCI name: Hydroxypropylcellulose, CAS No.: 9004-64-2). The water-soluble polymer suspension of hydroxypropylcellulose may be present in a concentration range of 3.5% to 6.5%, preferably 4.0% to 6.0%, most preferably 4.5% to 5.5%.

This embodiment may further comprise a over-the-counter antifungal agent in a concentration range of 1.0% to 25%, preferably 1.0% to 10%, most preferably 1.0% to 3.0%.

If desired, a penetration enhancer such as acetylcysteine, allantoin, sodium thioglycolate, and urea may be used in the present invention. The penetration enhancer may be present in a concentration range of 0.090% to 20%, preferably 0.90% to 10%, most preferably 3.0% to 5.0%.

If desired, antifungal essential oils such as camphor, eucalyptus, menthol, oregano, tea tree, and thymol may be used in the present invention. Antifungal aromatic molecules that make up chemotyped essential oils are phenols, terpenic alcohols, and aromatic aldehydes. The antifungal essential oil may be present in a concentration range of 0.10% to 6.0%, preferably 2.0% to 5.0%, most preferably 3.0% to 4.0%.

A further embodiment of the invention involves using Franz diffusion cells to measure active drug penetration of a composition as described herein. Franz Cells are individually hand blown diffusion cells made of two borosilicate glass components. The upper part may be called the cell cap, cell top, donor chamber, or donor compartment. The lower portion is generally called the body of the cell. Sometimes it is referred to as the receptor chamber but in the case of jacketed cells this is misleading as the receptor chamber is typically the innermost portion of the cell. Permeation studies using modified Franz diffusion cells and bovine hoof membranes as a model for the nail plate have been used to show enzyme enhanced drug permeation through a hoof membrane (International Journal of Pharmaceutics, Volume 332, Issues 1-2 pp. 196-201 (6 Mar. 2007)).

Methods

The fungus treatment composition may be prepared be blending the proper amounts and ratios of all the required ingredients together. This inorganic suspension can later be used to dissolve active drugs to make the final composition.

One embodiment of the invention would include preparation as follows:

Suspension Phase:
Into a tank, add Purified Water, USP. Turn on mixer at 5 RPM. Add VEEGUM HS. Increase mixer speed to 10 RPM and continue mixing for 30 minutes or until dissolved.

Aqueous Phase:
Into same tank, add Propylene Carbonate. Add Propylene Glycol. Add PRIMAFLO HP22. Add EDTA. Add Miconazole Nitrate. Add Allantoin. Add Sodium Thioglycolate. Maintain mixer speed at 10 RPM, and turn on sweeper at 25 RPM.

Oil Phase:
In same tank, add SD-40B Alcohol. Add Camphor. Add Eucalyptus Oil. Add Menthol. Add Urea. Add Oregano Oil. Add Tea Tree Oil. Add Thymol. Add Acetylcysteine. Maintain mixer speed at 10 RPM and sweeper speed at 25 RPM, and mix for 15 minutes.

Final Phase:
In same tank, add 50% Sodium Hydroxide. Maintain mixer speed at 10 RPM and sweeper speed at 25 RPM, and turn on homogenizer for 20 minutes.

Example 1

| Ingredient | Amount |
| --- | --- |
| Propylene Carbonate | 20.00 |
| Purified Water, USP | 20.00 |
| Propylene Glycol | 10.00 |
| EDTA | 0.06 |
| Miconazole Nitrate | 2.00 |
| Veegum HS | 5.00 |
| Allantoin | 13.00 |
| Sodium Thioglycolate | 5.20 |
| Camphor | 5.20 |
| Oregano Oil | 0.06 |
| Menthol | 5.20 |
| *Eucalyptus* Oil | 5.20 |
| Urea | 0.90 |
| Thymol | 0.06 |
| Tea Tree Oil | 0.06 |
| Acetylcysteine | 0.06 |
| PRIMAFLO HP22 | 5.00 |
| 50% Sodium Hydroxide | pH 3-9 |
| SIMULGEL NS | 3.00 |

This embodiment of the invention is prepared as follows:

Suspension Phase
Into a tank, add Purified Water, USP. Turn on mixer at 5 RPM. Add VEEGUM HS. Increase mixer speed to 10 RPM and continue mixing for 30 minutes or until dissolved.

Aqueous Phase
Into same tank, add Propylene Carbonate. Add Propylene Glycol. Add PRIMAFLO HP22. Add EDTA. Add Miconazole Nitrate. Add Allantoin. Add Sodium Thioglycolate. Maintain mixer speed at 10 RPM, and turn on sweeper at 25 RPM.

Oil Phase
In same tank, add Camphor. Add Eucalyptus Oil. Add Menthol. Add Urea. Add Oregano Oil. Add Tea Tree Oil. Add Thymol. Add Acetylcysteine. Maintain mixer speed at 10 RPM and sweeper speed at 25 RPM, and mix for 15 minutes.

Final Phase
In same tank, add SIMULGEL NS (Hydroxyethyl Acrylate/Sodium Acryloyldimethyl Taurate Copolymer and Squalane and Polysorbate 60, Seppic, Paris, France). Add 50% Sodium Hydroxide. Maintain mixer speed at 10 RPM and sweeper speed at 25 RPM, and turn on homogenizer for 20 minutes.

Example 2

A preferred embodiment of the invention for optimum drying and barrier properties was prepared containing the following ingredients:

| Ingredients | Amount |
| --- | --- |
| Propylene Carbonate | 12.30 |
| Purified Water, USP | 29.01 |
| Propylene Glycol | 8.30 |
| SD-40B Alcohol | 8.30 |
| EDTA | 0.10 |
| Miconazole Nitrate | 2.00 |
| VEEGUM HS | 4.10 |
| Allantoin | 16.50 |
| Sodium Thioglycolate | 2.30 |
| Camphor | 4.30 |
| Oregano Oil | 0.10 |
| Menthol | 2.30 |
| *Eucalyptus* Oil | 2.30 |
| Urea | 0.90 |
| Thymol | 0.10 |
| Tea Tree Oil | 0.10 |
| Acetylcysteine | 0.09 |
| PRIMAFLO HP22 | 4.10 |
| SIMULGEL NS | 2.50 |
| 50% Sodium Hydroxide | 0.30 |

This embodiment of the invention is prepared as follows:

Suspension Phase

Into a tank, add Purified Water, USP. Turn on mixer at 5 RPM. Add VEEGUM HS. Increase mixer speed to 10 RPM and continue mixing for 30 minutes or until dissolved.

Aqueous Phase

Into same tank, add Propylene Carbonate. Add Propylene Glycol. Add PRIMAFLO HP22. Add EDTA. Add Miconazole Nitrate. Add Allantoin. Add Sodium Thioglycolate. Maintain mixer speed at 10 RPM, and turn on sweeper at 25 RPM.

Oil Phase

In same tank, add SD-40B Alcohol. Add Camphor. Add Eucalyptus Oil. Add Menthol. Add Urea. Add Oregano Oil. Add Tea Tree Oil. Add Thymol. Add Acetylcysteine. Maintain mixer speed at 10 RPM and sweeper speed at 25 RPM, and mix for 15 minutes.

Final Phase

In same tank, add SIMULGEL NS. Add 50% Sodium Hydroxide. Maintain mixer speed at 10 RPM and sweeper speed at 25 RPM, and turn on homogenizer for 20 minutes.

Example 3

A preferred embodiment of the invention for pharmaceutically elegant properties was prepared containing the following ingredients:

| Ingredients | Amount |
| --- | --- |
| Propylene Carbonate | 13.60 |
| Purified Water, USP | 26.51 |
| Propylene Glycol | 9.10 |
| SD-40B Alcohol | 9.10 |
| EDTA | 0.10 |
| Miconazole Nitrate | 2.00 |
| VEEGUM HS | 5.00 |
| Allantoin | 18.20 |
| Sodium Thioglycolate | 1.20 |
| Camphor | 4.80 |
| Oregano Oil | 0.10 |
| Menthol | 2.60 |
| *Eucalyptus* Oil | 1.20 |
| Urea | 0.90 |
| Thymol | 0.10 |
| Tea Tree Oil | 0.10 |
| Acetylcysteine | 0.09 |
| PRIMAFLO HP22 | 5.00 |
| 50% Sodium Hydroxide | 0.30 |

This embodiment of the invention is prepared as follows:

Suspension Phase

Into a tank, add Purified Water, USP. Turn on mixer at 5 RPM. Add VEEGUM HS. Increase mixer speed to 10 RPM and continue mixing for 30 minutes or until dissolved.

Aqueous Phase

Into same tank, add Propylene Carbonate. Add Propylene Glycol. Add PRIMAFLO HP22. Add EDTA. Add Miconazole Nitrate. Add Allantoin. Add Sodium Thioglycolate. Maintain mixer speed at 10 RPM, and turn on sweeper at 25 RPM.

Oil Phase

In same tank, add SD-40B Alcohol. Add Camphor. Add Eucalyptus Oil. Add Menthol. Add Urea. Add Oregano Oil. Add Tea Tree Oil. Add Thymol. Add Acetylcysteine. Maintain mixer speed at 10 RPM and sweeper speed at 25 RPM, and mix for 15 minutes.

Final Phase

In same tank, add 50% Sodium Hydroxide. Maintain mixer speed at 10 RPM and sweeper speed at 25 RPM, and turn on homogenizer for 20 minutes.

REFERENCES CITED

The following references, to the extent that they provide exemplary procedural or other details supplementary to those set forth herein, are specifically incorporated herein by reference.

U.S. Patent Documents

U.S. Pat. No. 5,696,164 to Sun, et al., issued Dec. 9, 1997
U.S. Pat. No. 5,814,305 to Laugier, et al., issued Sep. 29, 1998
U.S. Pat. No. 5,993,790 to Strauss, et al., issued Nov. 30, 1999
U.S. Pat. No. 6,042,845 to Sun, et al., issued Mar. 28, 2000
U.S. Pat. No. 6,143,793 to Laugier, et al., issued Nov. 7, 2000
U.S. Pat. No. 6,224,887 to Samour, et al., issued May 1, 2001
U.S. Pat. No. 6,284,258 to Rose, et al., issued Sep. 4, 2001
U.S. Pat. No. 6,296,838 to Bindra, et al., issued Oct. 2, 2001
U.S. Pat. No. 6,455,592 to Laugier, et al., issued Sep. 24, 2002
U.S. Pat. No. 6,495,124 to Samour, et al., issued Dec. 17, 2002
U.S. Pat. No. 6,676,953 to Hexamer, et al., issued Jan. 13, 2004
U.S. Pat. No. 7,048,913 to Hexamer, et al., issued May 23, 2006
U.S. Pat. No. 7,074,392 to Friedman, et al., issued Jul. 11, 2006

Foreign Patent Documents

International Patent No. WO/2002/022115 to McKenzie, et al., issued Mar. 21, 2002

References

Academy of Pharmaceutical Sciences Conference, 2005
Aly, R. 1999. Ecology, epidemiology and diagnosis of tinea capitis. Pediat Inf. Dis J. 18:180-185
Aly, R., R. J. Hay, A. Del Palacio, and R. Galimberti. 2000. Epidemiology of tinea capitis. Med Mycol. 38:183-188
Aman, S., T. S. Haroon, I. Hussain, M. A. Bokhari, and K. Khurshid. 2001. Tinea unguium in Lahore, Pakistan. Med Mycol. 39:177-180
British Journal of Dermatology, Volume 85 Issue 5 Page 437-449, November 1971
Chem Pharm Bull (Tokyo). 1998 November; 46(11):1797-802
DIFLUCAN (fluconazole) (Pfizer, New York) Capsule Prescribing Information
FULVICIN (griseofulvin) (Schering-Plough, Kenilworth, N.J.) Tablet Prescribing Information
Grieve, Maud (Mrs.). Thyme. A Modern Herbal. Hypertext version of the 1931 edition. Accessed: Dec. 14, 2006
Indian J Pathol Microbio. 2002 April; 45(2):169-72
Int J Pharm. 2002 Oct. 1; 245(1-2):25-36
International Journal of Pharmaceutics, 2007 March 6; 322 (1-2):196-201

Journal of the American Podiatric Medical Association, Vol 89, Issue 3 124-130, 1999
J Invest Dermatol. 1981 February; 76(2):76-9
J Pharm Pharmacol. 1983 January; 35(1):28-33
J Pharm Pharmacol. 1985 November; 37(11):771-5
J Pharm Pharmacol. 1999 March; 51(3):271-8
Kwon-Chung, K. J., and J. E. Bennett. 1992. Medical Mycology. Lea & Febiger, Philadelphia
LAMISIL (terbinafine HCl) (Novartis, Basel, Switzerland) Tablet Prescribing Information
Nail Swelling as a Pre-formulation Screen for the Selection and Optimisation of Ungual Penetration Enhancers, Journal of Pharmaceutical Research, July 2007
PENLAC Nail Lacquer (ciclopirox) (Sanofi-Aventis, Bridgewater, N.J.) Topical Solution, 8% Prescribing Information
Phytother Res. 2003 April; 17(4):376-9
Ramsewak R S, et al. In vitro antagonistic activity of monoterpenes and their mixtures against 'toe nail fungus' pathogens. Phytother Res. 2003 April; 17(4):376-9
Robbins C R. Chemical & Physical behavior of human nail, 3rd edition, New York: Springer-verlag 1997 pp-93-130
SPORANOX (itraconazole) (Janssen-Ortho, Raritan, N.J.) Oral Solution Prescribing Information
"The Cure is in the Cupboard: How to Use Oregano for Better Health" by Dr. Cass Ingram
*Thymus Vulgaris*. PDR for Herbal Medicine. Montvale, N.J.: Medical Economics Company. p. 1184
Weitzman, I., and R. C. Summerbell. 1995. The dermatophytes. Clin Microbiol Rev. 8:240-59

What is claimed:

1. A fungus treatment composition consisting of:
   a smectite clay;
   a water-miscible solvent;
   a water-soluble polymer;
   an antifungal agent;
   a penetration enhancer; and
   an antifungal essential oil;
   wherein the penetration enhancer is a compound selected from the group consisting of: from about 0.01 percent to about 0.09 percent of acetylcysteine, from about 1.0 percent to about 20 percent of allantoin, from about 1.0 percent to about 10 percent of sodium thioglycolate, and from about 0.1 percent to about 0.9 percent of urea, or a mixture thereof; and
   wherein the antifungal essential oil is from about 1 percent to about 10 percent and is a reagent selected from the group consisting of: a phenol, a terpenic alcohol, and an aromatic aldehyde, or a mixture thereof.

2. The fungus treatment composition of claim 1, wherein the smectite clay consists of montmorillonite or bentonite.

3. The fungus treatment composition of claim 1, wherein the water-miscible solvent is selected from the group consisting of: ethylene glycol, 1,2-propylene glycol, 1,3-propanediol, 1,2-butylene 2,3-butylene glycol, 1,4-butanediol, 1,2-hexylene glycol, diethylene glycol, dipropylene glycol, polyethylene glycol, polypropylene glycol, glycerin, trimethylolpropane, pentaerythritol, sorbitol, diethyl carbonate, diisopropyl carbonate, dibutyl carbonate, ethylene carbonate, propylene carbonate, 1,2-butylene carbonate, 2,3-butylene carbonate, methanol, ethanol, 1-propanol, 2-propanol, 2-methyl-1-propanol, 1-butanol, 2-butanol, 2-methyl-2-propanol, 2-propene-1-ol, 2-propyn-1-ol, 2-methoxy-1-ethanol, 1-methoxy-2-propanol, and 2-methoxy-1-propanol, or a mixture thereof.

4. The fungus treatment composition of claim 1, wherein said water-miscible solvent is in an amount ranging from about 5 percent to about 30 percent.

5. The fungus treatment composition of claim 1, wherein the water-soluble polymer consists of a hydroxypropylcellulose.

6. The fungus treatment composition of claim 1, wherein the antifungal agent consists of clioquinol, haloprogin, miconazole nitrate, povidone-iodine, tolnaftate, undecylenic acid, calcium undecylenate, copper undecylenate, or zinc undecylenate.

7. The fungus treatment composition of claim 1, wherein said antifungal agent is in an amount ranging from about 1.0 percent to about 25 percent.

8. A method of testing nail penetration of an active drug in the fungus treatment composition of claim 1 comprising:
   using Franz diffusion cells and nail pieces to measure the active drug penetration from the fungus treatment composition.

* * * * *